United States Patent [19]
Kotzin et al.

[11] Patent Number: 5,336,598
[45] Date of Patent: Aug. 9, 1994

[54] METHOD FOR DIAGNOSING A SUPERANTIGEN CAUSED PATHOLOGIAL CONDITION VIA ASSAY OF T-CELLS

[75] Inventors: Brian L. Kotzin; Philippa Marrack; John Kappler; Youngwon Choi, all of Denver, Colo.

[73] Assignee: National Jewish Center for Immunology and Respiratory Medicine, Denver, Colo.

[21] Appl. No.: 437,370

[22] Filed: Nov. 15, 1989

[51] Int. Cl.$^5$ .................. C12Q 1/68; G01N 33/577
[52] U.S. Cl. ...................... 435/7.24; 435/6; 436/501; 436/548
[58] Field of Search ............ 435/6, 7.24; 436/506, 436/548, 501

[56] References Cited

U.S. PATENT DOCUMENTS

| | | | |
|---|---|---|---|
| 4,677,061 | 6/1987 | Rose et al. | 435/7.24 |
| 4,683,195 | 7/1987 | Mullis et al. | 436/63 |
| 4,886,743 | 12/1989 | Hood et al. | 436/506 |

OTHER PUBLICATIONS

Kotzin et al., J. Immunol. 143: 89–94 (Jul. 1, 1989).
Finkel et al., Cell 58: 1047–1054 (Sep. 22, 1989).
Choi et al., Proc. Natl. Acad. Sci. USA 86: 8941–8945 (Nov. 1989).
Pullen et al., J. Immunol. 142: 3033–3037 (May 1, 1989).
White et al., Cell 56: 27–35 (Jan. 13, 1989).
Pullen et al., Immunol. Rev. 107: 125–139 (Feb. 1989).
Marrack et al., Nature 328: 503–555 (Apr. 6, 1989).
Blackman et al., Science 244: 214–217 (Apr. 14, 1989).
Kubo et al., J. Immunol. 142: 2736–2442 (Apr. 15, 1989).
Kappler et al., J. Exp. Med. 169: 1522–1541 (May 1989).
Finkel et al., J. Immunol. 142: 3033–3037 (May 1, 1989).
Kappler et al., Science 244: 811–813 (May 19, 1989).
C. A. Janeway, Jr. et al, *Immunol. Rev.*, 107, 61–88, 1989.

*Primary Examiner*—David Saunders
*Attorney, Agent, or Firm*—Beaton & Swanson

[57] ABSTRACT

The invention teaches a method for determining levels of T-cell surface antigens in humans, specifically, V$\beta$ molecules. Measurement of such levels allows for diagnosis of pathological conditions, such as infections, where changes in these levels are indicative of a superantigen initiated pathological condition.

4 Claims, 5 Drawing Sheets

METHOD FOR DIAGNOSING A SUPERANTIGEN CAUSED PATHOLOGIAL CONDITION VIA ASSAY OF T-CELLS

FIELD OF THE INVENTION

This invention relates to a method for diagnosing a pathological condition, via assaying or measuring particular T-cell subtypes in a sample taken from a patient suspected of having the pathological condition. In particular, it relates to measuring cell surface antigens of T-cells which are characteristic of particular T-cell subtypes.

RELATED PUBLICATION

Portions of the invention described herein have been presented in Kappler, et al., Science 244: 811–813 (May 19, 1989), the inventors' publication and the disclosure of which is incorporated by reference herein.

BACKGROUND AND PRIOR ART

In recent years, the mechanism by which mammalian immune systems, such as human and murine systems react to infections, foreign antigens, and to so-called "self antigens" in connection with autoimmune diseases has begun to be established. See, in this regard, Grey, et al., Scientific American 261(5): 56–64 (1989); Male, et al., *Advanced Immunology* (J. P. Lippincott Company, 1987), especially chapters 6 through 10.

Well known, both to the skilled artisan and to the general public is the role of antibodies, sometimes referred to as "immunoglobulin" or the less correct and older "gammaglobulin" in response to infection. Antibodies are protein molecules which are produced by B cells in response to infection. It is well known that these antibodies act to "disable" or to inactivate infectious agents in the course of combating the infection.

In order for antibodies to be produced, however, preceding events must occur which lead to stimulation of the B cells which produce the antibodies. One of the key events involved in the processes leading to antibody production is that of antigen recognition. This aspect of the immune response requires the participation of so-called "T-cells", and is less well known than the antibody response commented on supra.

Briefly, and in outline form, antigen recognition requires interaction of an "antigen presentation cell", a "processed antigen", and a T-cell. See Grey and Male, supra. The "processed antigen", in an infection, is a molecule characteristic of the pathogen which has been treated, i.e., "processed", by other cells which are a part of the immune system. The processed antigen interacts with a receptor on the surface of an antigen presented in a manner not unlike a lock fitting into a key hole or, perhaps more aptly, two pieces of a jigsaw puzzle.

The configuration of the complex of processed antigen and receptor on antigen presentation cell allows the participation of T-cells. T-cells do not join the complex unless and until the processed antigen has fit into the receptor on the antigen presentation cell. This receptor will hereafter be referred to by its scientific name, the major histocompatibility complex (MHC), or the human leukocyte antigen (HLA). Generally, MHC is used to refer to murine systems, and HLA to humans.

These receptors fall into two classes. MHC-II molecules are involved in most responses to pathogens. In contrast, MHC-I molecules are involved when the pathogen is a virus, or a malignant cell is involved.

When MHC-I participation is involved, there is no antibody stimulation; rather, the interaction of MHC-I, processed antigen and T-cell leads to lysis of cells infected with the pathogen.

The foregoing discussion has focused on the events involved in responding to "infection", i.e., the presence of pathogenic foreign material in the organism. Similar mechanisms are involved in autoimmune diseases as well. In these conditions, the organism treats its own molecules as foreign, or as "self-antigens". The same type of complexing occurs as described supra, with an antibody response being mounted against the organism itself. Among the diseases in which this is a factor are rheumatoid arthritis, diabetes, systemic lupus erythematosis, and others.

The ability of the T-cell to complex with the processed antigen and MHC/HLA complex is dependent on what is referred to as the T-cell antigen receptor, referred to as "TCR" hereafter. The TCR is recognized as a heterodimer, made up of alpha ($\alpha$) and beta ($\beta$) chains. Five variable elements, coded for by germline DNA and known as "V$\alpha$, J$\alpha$, V$\beta$, D$\beta$, and J$\beta$" as well as non-germline encoded amino acids contribute to the TCR. See, in this regard, Marrack, et al., Immunol. Today 9: 308–315 (1988); Toyonaga, et al., Ann. Rev. Immunol 5: 585–620 (1987); Davis, Ann. Rev. Immunol 4: 529–591 (1985); Hendrick, et al., Cell 30: 141–152 (1982). With respect to the binding of TCR with processed antigen and MHC, see Babbitt, et al., Nature 317: 359–361 (1985); Buus, et al., Science 235: 1353–1358 (1987); Townsend, et al., Cell 44: 959–968 (1986); Bjorkman, et al., Nature 329: 506–512 (1987).

Generally, both the alpha and beta subunits are involved in recognition of the ligand formed by processed antigen and MHC/HLA molecule. This is not always the case, however, and it has been found that so-called "superantigens" stimulate T-cells with a particular V$\beta$ element, regardless of any other element. See Kappler, et al., Cell 49: 273–280 (1987); Kappler, et al., Cell 49: 263–271 (1987); MacDonald, et al., Nature 332: 40–45 (1988); Pullen, et al., Nature 335: 796–801 (1988); Kappler, et al., Nature 332: 35–40 (1988); Abe, et al., J. Immunol 140: 4132–4138 (1988); White, et al., Cell 56: 27–35 (1989); Janeway, et al., Immunol. Rev. 107: 61–88 (1989); Berkoff, et al., J. Immunol 139: 3189–3194 (1988), and Kappler, et al., Science 244: 811–813 (1989). This last reference discloses information which is also incorporated into the subject patent application.

The "superantigens" mentioned supra, while generally stimulating T-cells as long as they possess a V$\beta$ element, are somewhat specific in terms of the particular form of the V$\beta$ moiety which is present on the stimulated T cell. This feature is one aspect of the invention, i.e., the ability to assay for particular subtypes or subclasses of T-cells, based upon the cell surface antigens presented by these subclasses.

*Staphylococcus aureus* has long been implicated in morbidity and mortality in humans. See Bergdoll, in *Feed Bourne Infections and Intoxications* (Riemann and Bryan, ed., Acad. Press, N.Y.) pp. 443–494 (1979). The various toxins presented by *S. aureus* are responsible for most food poisoning cases, as well as severe shock, and other life threatening pathological conditions. The mechanism of action of the toxins associated with S. aureus is unknown. The primary structure of the toxins, while showing some relationship, also show some great differences in primary structure. See Betley, et al., J.

Bacteriol 170: 34–41 (1988); Jones, et al., J. Bacteriol 166: 29–33 (1986); Lee, et al., J. Bacteriol 170: 2954–2960 (1988); Blomster-Hautamaa, et al., J. Biol. Chem. 261: 15783–15786 (1986). For the time being, it cannot be said with any certainty whether the various S. aureus antigens function in the same way in terms of the immunological response they generate.

The ability of S. aureus to stimulate powerful T cell proliferative responses in the presence of mouse cells bearing MHC-II type molecules is taught by, e.g., Carlson, et al. J. Immunol 140-2848 (1988); White, et al., Cell 56 27–35 (1989); Janeway, et al., Immunol. Rev. 107:61–88 (1989). White, et al., and Janeway, et al. showed that one of these proteins is not mitogenic, in that it selectively stimulates murine cells which bear particular V$\beta$ elements. These papers, however, did not extend the study to human cells. It has now been shown, however, that certain antigens do selectively stimulate specific V$\beta$ subclasses of human T cells, making it possible to diagnose pathological conditions by assaying for particular V$\beta$ subtypes.

Hence, it is an object of the invention to describe a method for diagnosing a pathological condition in a human by assaying a biological sample from the subject being tested for levels of particular V$\beta$ subtypes. These levels are then compared to normal levels, where a difference between the two is indicative of a pathological condition.

It is a further object of the invention to carry out the assaying using antibodies which are specific for the particular V$\beta$ subtype. Especially preferred are monoclonal antibodies.

It is still another object of the invention to perform the above described assay by measuring DNA coding for specific V$\beta$ molecules. This can be done via utilizing, e.g., the polymerase chain reaction.

How these and other objects of the invention are achieved are detailed in the disclosure which follows.

DETAILED DESCRIPTION OF PREFERRED EMBODIMENTS

Example 1

This experiment used monoclonal antibodies directed against V$\beta$5, V$\beta$6, V$\beta$8 and V$\beta$12, as taught by Yssel, et al., Eur. J. Immunol. 16: 1187 (1986); Borst, et al., J. Immunol. 139: 1952 (1987); Posnett, et al., Proc. Natl. Acad. Sci. USA 83: 7888 (1986); Carrel, et al., Eur. J. Immunol 16: 649 (1986), and Bigler, et al., J. Exp. Med. 158: 1000 (1983).

T cells of a human individual were first isolated from that individual's peripheral blood. These T cells were then examined before and after stimulation with one of (i) anti-CD3 antibody, (ii) SEC2; (iii) SED, or (iv) SEE. Items (ii), (iii) and (iv) are known S. aureus molecules which act as toxins.

The anti-CD3 antibodies had been rendered stimulatory by adherence to plastic bottles. The protein was incubated on plastic surfaces for 8 hours at 4° C. Extensive washing removed non-adherent antibody. Following this, either adherent antibody or a S. aureus antigen was used to stimulate peripheral blood T cells.

Stimulation took place in the presence of irradiated, autologous, non T-cells as described by Kotzin, et al., J. Immunol. 127: 931 (1981), the disclosure of which is incorporated by reference herein.

Three days after stimulation, live cells were collected and cultured for 24 hours in recombinant human IL-2 (25 units/ml). This allows regeneration of potentially modified receptors. Of the surviving cells, about 10% were true blast cells.

The blast cell fractions were then incubated with one of (i) purified antibody to CD3 or with a monoclonal antibody to (ii) V$\beta$5 (mAb 1C1); (iii) V$\beta$6 (mAb OT145); (iv) V$\beta$8 (mAb MX6), or (v) V$\beta$12 (mAb S511). Following incubation with the mAb, the cells were stained with fluorescein-conjugated goat anti mouse IgG, following Kappler, et al., Cell 49: 173 (1987). The staining pattern was then studied on an EPICS C device, using a forward angle and 90° light scatter pattern to gate large blast cells, which were easily distinguished from small lymphocytes, and constituted 50% or more of all surviving cells in culture.

Figure 1:
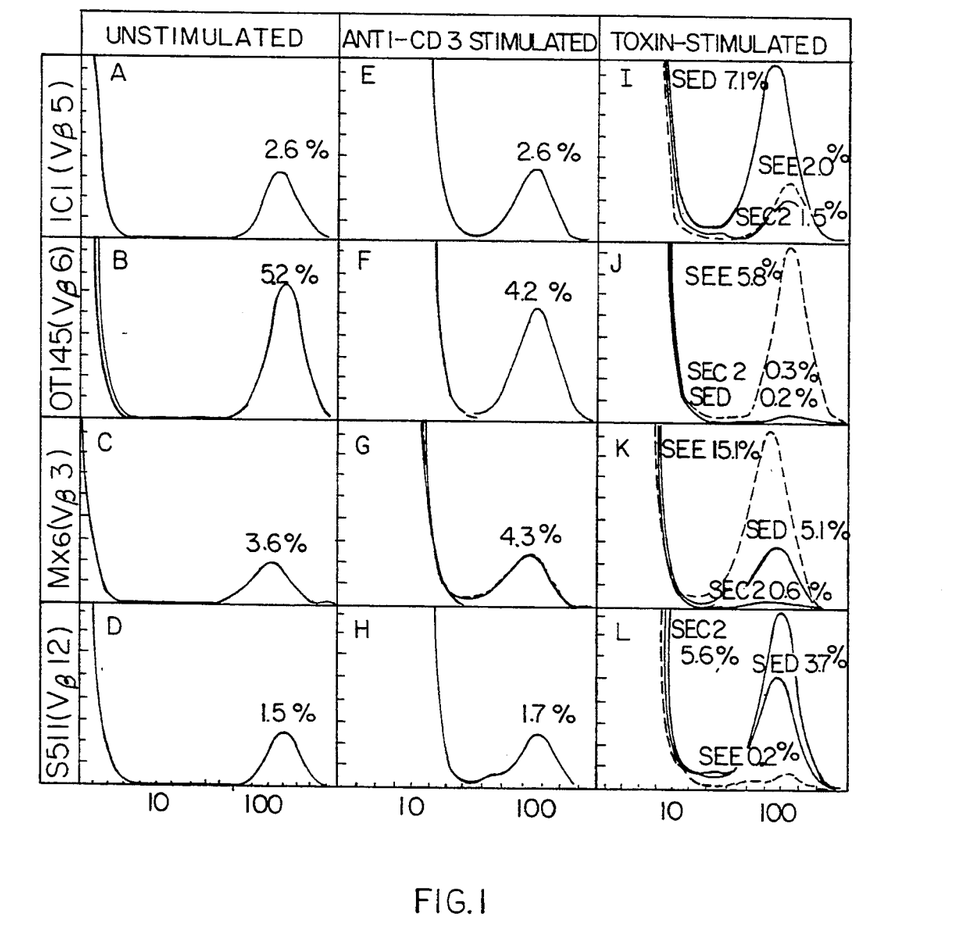
FIG. 1 shows the results of staphylococcal toxin stimulation of human T cells.

The results of the staining patterns are shown in FIG. 1. Panels A–D shows the degree of staining using the mAbs before stimulation. Panels E–H show it after stimulation with anti-CD3. Finally, panels I–L show the pattern following stimulation with SED, SEE, and SEC2.

Each anti-V$\beta$ stained a definable percentage of the peripheral resting T cells from this donor (FIG. 1). The percentage stained ranged from 5.2% with anti-V$\beta$6 to 1.5% with anti V$\beta$12 (FIG. 1, A to D). Culture with anti-CD3 and interleukin-2 hardly changed the percentage stained with each anti-V$\beta$ (FIG. 1, E to H), indicating that this combination of T cell stimuli affected T cells bearing different $\alpha\beta$ receptors similarly. Culture with the toxins had variable effects on the percentage of T cells stained with each anti-V$\beta$ (FIG. 1, I to L) Staphylococcal entertoxin (SE) D, for example, greatly increased the percentage of T cells bearing V$\beta$5 in the blast population and nearly excluded cells bearing V$\beta$6. In contrast, T cells blasts stimulated with SEC2 were depleted of V$\beta$6- and V$\beta$8 bearing T cells and were greatly enriched in V$\beta$12 bearing T cells. Finally, SEE stimulated V$\beta$8+ T cells, while excluding cells bearing V$\beta$12. Reciprocal results for each of the toxins were found if the resulting T cells contaminating the blast populations were analyzed for V$\beta$ usage. After SEE stimulation, for example, the resting T cells were selectively depleted of V$\beta$8+ cells. This result indicates that the toxins are stimulating most of the T cells bearing the appropriate V$\beta$s, nor a minor population of these cells.

Five different donors were used in the experiments. These donors were HLA-typed by standard serological techniques, and their restring peripheral T cells were stained with anti-CD3 and the anti-V$\beta$s. Each of the anti-V$\beta$s reacted with a low but measurable percentage of peripheral blood T cells from each of the individuals (Table 1). For a particular individual these percentages were extremely reproducible from one day to another.

The percentages of T cells that bore the different Vβs varied somewhat among individuals.

TABLE 1

Vβ expression on unstimulated human peripheral T cells.

| Cell donor | HLA type | | | | | Percentage of T cells bearing | | | |
|---|---|---|---|---|---|---|---|---|---|
| | A | B | C | DR | DQ | Vβ5 | Vβ6 | Vβ8 | Vβ12 |
| BK | 26 | 14 | | 1.4 | w1 | 3.9 | 3.3 | 3.2 | 1.3 |
| | 28 | 38 | | w53 | w3 | | | | |
| CW | 24 | 7 | 3 | 4.6 | w3 | 2.7 | 2.0 | 4.0 | 1.5 |
| | 31 | 60 | 7 | w52, w53 | | | | | |
| LS | 2 | 8 | w7 | 3.6 | w1 | 2.6 | 5.2 | 3.6 | 1.5 |
| | | 62 | | w52 | | | | | |
| RC | 1 | 35 | w4 | 1.7 | w1 | 3.2 | 6.1 | 6.5 | 1.2 |
| | 11 | 37 | | w53 | w2 | | | | |
| SL | 1 | 8 | w7 | 3.6 | w1 | 3.1 | 4.4 | 3.7 | 1.8 |
| | | 63 | | w52 | w2 | | | | |

Example 2

Figure 2:
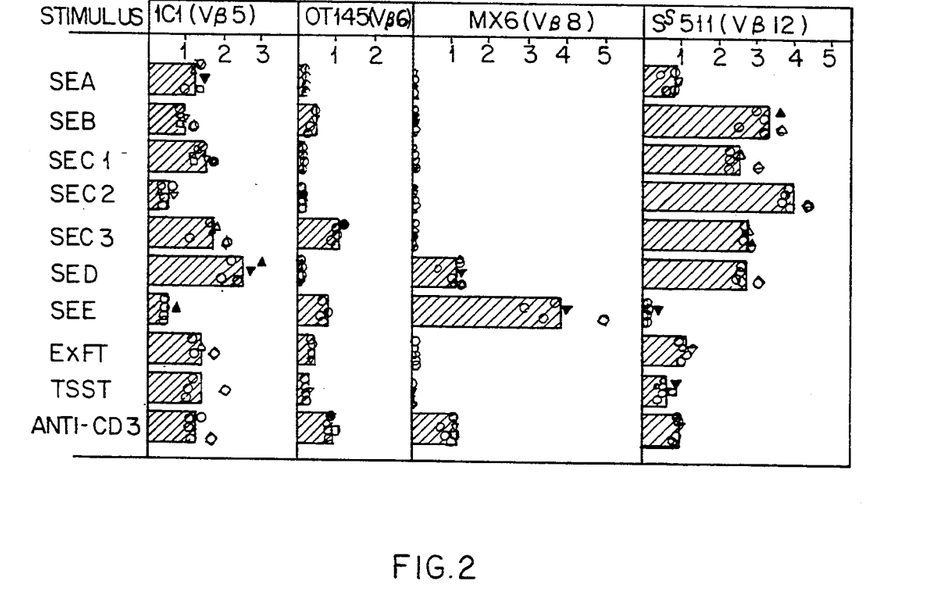
FIG. 2 depicts studies showing V$\beta$ specific stimulation of T cells by toxins is donor independent.

Cells from the different donors were stimulated with anti-CD3 or the staphylococcal toxins and analyzed for CD3 and Vβ expression (FIG. 2). For each individual, results were calculated as the percentage of T cell blasts bearing a particular Vβ after stimulation divided by the percentage of T cells bearing that Vβ before stimulation. This calculation was designed to correct for variations in Vβ expression from one person to another. As before, anti-CD3 stimulated T cells bearing the different Vβs uniformly; the ratio of T cells bearing a particular Vβ before and after CD3 stimulation was close to 1. In contrast, it was clear that the staphylococcal toxins varied markedly in their ability to stimulate T cells bearing different Vβs. For example, T cells bearing Vβ5 and Vβ12 were quite rich in blasts produced by challenge with SEC3, whereas T cells bearing Vβ8 were specifically excluded from the SEC3 blasts. One or more of the toxins was a stimulus for T cells positive for each of the Vβ families (albeit weakly for Vβ6), indicating that a toxin superantigen had been identified for each of the Vβ families. Conversely, toxins could be identified which specifically failed to stimulate T cells bearing each of the Vβs.

It is remarkable that a characteristic stimulation pattern could be identified for almost each toxin. SEC2, for example, stimulated T cells bearing Vβ12 and excluded cells bearing Vβs from the other three families. This pattern was not seen with any of the other toxins. SED stimulated T cells bearing Vβ5 and Vβ12, had marginal effects on T cells bearing Vβ8, and excluded cells bearing Vβ6. Again, this pattern was unique to this toxin.

In some cases, stimulation with a given enterotoxin yielded blasts that were neither enriched nor depleted for expression of a given Vβ by comparison with the starting population. Starting and ending percentages of Vβ5-bearing cells were similar, for example, in responses to toxic shock toxin (TSST). Such a result might indicate that only some Vβ5-bearing T cells were stimulated by TSST. Perhaps the other variable components of the receptor, Vα, Jα, or Jβ, could quite often prevent interaction of this toxin with Vβ5, a phenomenon that has been noticed before for superantigen reaction with mouse T cell receptor Vβs. Alternatively, TSST may react with only one member of the Vβ5 family. Thus, in responses to TSST, the increase in blasts bearing this member may be offset by a disappearance of T cells bearing other members of the family, but also reactive with 1C1. Discrimination by superantigens among different members of Vβ families has been seen in mice, where the self superantigen Mls-1 stimulates T cells positive for Vβ8.1 but not those bearing Vβ8.2 or Vβ8.3 (Kappler, et al. Nature 332: 35 (1988), and SEC1 stimulates T cells bearing Vβ8.2 but not those bearing Vβ8.1 or Vβ8.3.

In some experiments, the percentages of T cells that stained with anti-CD4 or anti CD9 were checked before and after stimulation. The starting percentages were virtually unchanged by toxin stimulation. T cells from one donor, for example, were initially 78% CD4+ and 23% CD8+. After stimulation with the nine different toxins the percentages in the blast of CD4+ cells ranged from 74% to 79%, and of CD8+ cells from 20% to 25%, suggesting that all these stimuli affected CD4 and CD8 cells equally. It might have been expected that the toxins, which are dependent on class II MHC for presentation would have preferentially stimulated CD4+ cells, but such is not the case.

One of the most striking features of the data in FIG. 2 is the consistency of the results from one individual to another. Thus, although the five people tested had different HLA types and different starting percentages of T cells bearing the various Vβs (Table 1), the proportional changes in Vβ expression in blasts stimulated by each toxin were almost the same from one individual to another. Although the superantigens require class II MHC for presentation, the allele of class II has much less impact on superantigen presentation than it does on recognition of conventional antigens plus MHC by T cells.

These results show that the staphylococcal toxins are not indiscriminate mitogens for human T cells, but are, in fact, Vβ-specific. This result accounts for the previously noted clonal specificity for such toxins. Although each toxin is able to stimulate only a subpopulation of all T cells in humans, they are still powerful T cell stimulants, active at low concentrations. Some or all of the toxic effects of these proteins in humans may be mediated by their ability to stimulate large numbers of human T cells. For example, the ability of these toxins to induce secretion of large quantities of lymphokines is probably secondary to their ability to stimulate, in a Vβ-specific way, a sizable percentage of T cells. It is also possible that the ability of these and other microbial-derived superantigens to stimulate populations of T cells bearing particular Vβs may be related to the differential resistance of different individuals to the effects of these toxins and also to the ability of microbial attack to induce immune consequences, such as autoimmunity, in certain individuals.

Example 3

The foregoing examples demonstrated a method for quantifying T cell subsets having particular cell surface phenotypes, using antibodies. This methodology calls for interaction between the antibody and its binding partners, i.e., the cell surface antigen, which is the Vβ molecule.

Enhanced presence of the Vβ molecules means that there has been enhanced expression of the DNA coding for the particular molecule. Thus, the following experiments deal with the measurement of the aforementioned T-cell subsets via analysis of the DNA expressing a particular Vβ subtype.

Among the methods available to the skilled artisan for analyzing DNA is the so-called polymerase chain reaction, or "PCR" as used hereafter. PCR methodology is well known to the art, as may be seen in, e.g, U.S. Pat. Nos. 4,683,195, 4,683,202 and 4,800,159, Saiki, et al., Science 239: 487–491 (1988), and Chelly, et al., Nature 333: 858–860 (1988). Given that the PCR methodology is known to the art, only the modifications to the technology used are elaborated upon.

Total RNA was prepared from anti-CD3 stimulated peripheral T cells as described supra. Two μg of total RNA was used for the synthesis of first strand cDNA using reverse transcriptase (Amersham) and random hexanucleotides. The reaction was stopped by heating for 5 minutes at 95° C. before polymerase chain reaction.

One twentieth of each cDNA samples was co-amplified using a Vβ-specific primer with a Cβ primer and two Cα primers as set forth at Table 2 with final concentration of 0.3 μM in each reaction. The amplification was performed with 2.5 U of Taq polymerase (Perkin-Elmer) and a Cetus Perkin Elmer thermocycler under the following conditions; 95° C. melting, 55° C. annealing, and 72° C. extension for 1 minute each. For quantification of amplified products, coamplification was performed with 5' $^{32}$P-labelled reverse primers (about $5 \times 10^5$ cpm each) The amplified products were separated on 2% agarose gels, dried and exposed to X-ray film. The autoradiograms were used to identify and cut out the Vβ-Cβ and Cα bands. Each band was counted by liquid scintilation counter. In control experiments, the relative amplification efficiency was calculated essentially as described by Chelly et al., supra.

5' sense primers for PCR were synthesized. Their sequences, and the Vβ's which they would be expected to amplify, are shown in Table 2. All the Vβ's indicated as amplified have sequences matching their corresponding primers exactly. There may have been other Vβ genes amplified with these primers. For example, the Vβ6 primer matches Vβ6.4 except for one nucleotide, and further experiments will be needed to find out if Vβ6.4 is amplified using this primer. Altogether, all these primers would be expected to cover at least 39 of the 46 sequenced human genes. Each Vβ specific oligomer was picked to have roughly the same G+C content and to be located at relatively the same position in Vβ.

Example 4

Total RNA was prepared from human peripheral T cells stimulated by anti-CD3 antibody or one of 5 different *S. aureus* toxins (SEB, SEC2, SEE, exfoliating toxin (ExT), and toxic shock syndrome toxin 1 (TSST), as described in the previous examples. At the time of analysis these populations contained 50–90% T cell blasts as judged by flow cytometric analysis. A single strand complementary DNA was prepared for mRNA phenotyping, following Buus, et al., Science 235: 1353–1358 (1987); Townsend, et al., Cell 44: 959–968 (1986), and aliquots of cDNA from each sample were amplified with each of the 22 5' Vβ specific sense primers and the 3' Cβ specific antisense primer. As an internal control, TCR α chain mRNA was co-amplified in the same tube. Amplification was performed with 25 cycles, a limited

TABLE 2

| Sequences of primers used for PCR | | |
|---|---|---|
| primer | sequence 5' → 3' | members[a] |
| Vβ1 | GCACAAACAGTTCCCTGACTTGCAC | 1.1, 1.2 |
| Vβ2 | TCATCAACCATGCAAGCCTGACCT | 2.1, 2.2, 2.3 |
| Vβ3 | GTCTCTAGAGAGAAGAAGGAGCGC | 3.1, 3.2 |
| Vβ4 | ACATATGAGAGTGGATTTGTCATT | 4.1, 4.2, 4.3 |
| Vβ5.1 | ATACTTCAGTGAGACACAGAGAAAC | 5.1 |
| Vβ5.2/3 | TTCCCTAACTATAGCTCTGAGCTG | 5.2, 5.3 |
| Vβ6 | AGGCCTGAGGGATCCGTCTC | 6.1, 6.2, 6.3 |
| Vβ7 | CCTGAATGACCCAACAGCTCTC | 7.1, 7.2 |
| Vβ8 | ATTTACTTTAACAACAACGTTCCG | 8.1, 8.2, 8.3, 8.4 |
| Vβ9 | CCTAAATCTCCAGACAAAGCTCAC | 9.1 |
| Vβ10 | CTCCAAAAACTCATCCTGTACCTT | 10.1, 10.2 |
| Vβ11 | TCAACAGTCTCCAGAATAAGGACG | 11.1, 11.2 |
| Vβ12 | AAAGGAGAAGTCTCAGAT | 12.1, 12.2 |
| Vβ13.1 | CAAGGAGAAGTCCCCAAT | 13.1[b] |
| Vβ13.2 | GGTGAGGGTACAACTGCC | 13.2[c] |
| Vβ14 | GTCTCTCGAAAAGAGAAGAGGAAT | 14.1[d] |
| Vβ15 | AGTGTCTCTCGACAGGCACAGGCT | 15.1 |
| Vβ16 | AAAGAGTCTAAACAGGATGAGTCC | 16.1 |
| Vβ17 | CAGATAGTAAATGACTTTCAG | 17.1 |
| Vβ18 | GATGAGTCAGGAATGCCAAAGGAA | 18.1 |
| Vβ19 | CAATGCCCCAAGAACGCACCCTGC | 19.1 |
| Vβ20 | AGCTCTGAGGTGCCCCAGAATCTC | 20.1 |
| 3'Cβ | TTCTGATGGCTCAAACAC | |
| 5'Cα | GAACCCTGACCCTGCCGTGTACC | |
| 3'Cα | ATCATAAATTCGGGTAGGATCC | |

Notes to Table 2
The size of amplified products (Vβ bands) by Vβ and 3'Cβ primers ranged from about 170 to 220 bp. The size of the amplified cDNA (Cα band) by 5'Cα and 3'Cα primers was about 600 bp. The 3'Cβ primer used in this study matches exactly both Cα 1 and Cα 2 DNA. The sequences of Vβ, Cβ, and Cα are from previously published reports.
[a] Members of each Vβ family which have identical sequences as the corresponding primer are listed.
[b] Vβ 13.1, [c] Vβ 13.2, and [d] Vβ 14.1 have also been called Vβ 12.3, 12.4, and 3.3, by Toyonaga, et al., Ann. Rev. Immunol. 5: 585–620 (1987), Kimura, et al., Eur. J. Immunol. 17: 375–383 (1987).

Among the at least 20 different families of human Vβ genes, at least 46 different members of these families have been cloned and sequenced, as reported by Toyonaga, et al., supra; Concannon, et al., Proc. Natl. Acad. Sci. USA 83: 6598–6602 (1986); Lai, et al., Nature 331: 543–546 (1988). To analyze human T cell Vβ usage, 22 different Vβ-specific oligonucleotides for use as number used to ensure that the amount of product synthesized was proportional to the amount of Vβ mRNA in the original preparation. The specificity of each Vβ specific primer was determined by the size of its amplified product and hybridization to the amplified products of specific probes (not shown). The amplification efficiencies of four of the primer sets (5'Cα-3'α, Vβs 2, 3, and 8-3'Cβ) were determined as described by Chelly, et al., supra. The average efficiency ranged about 46–48%. For each sample the number of counts in the Vβ band were normalized to those found in the Cα band.

It was necessary to find out whether or not the relative incorporation in this PCR reaction was proportional to the number of cells in the responding population expressing a particular Vβ element. However, two possible sources of error had to be considered. The first of these was contribution from unstimulated T cells. It was reasoned that, since mRNA levels are extremely low in unstimulated T cells compared to T cell blasts, the contribution from unstimulated cells would only become a problem when the proportion of blasts expressing a particular Vβ was very low compared to the unstimulated cells. Secondly, since all T cells have the potential to rearrange the β-locus on both chromosomes, transcription of Vβ mRNA from a non-productively rearranged chromosome in at least some T cells might confuse the analysis. Since non-functional mRNA could be expected to be at a low level due to its instability, it was reasoned that this mRNA may only present a problem in cases where a particular Vβ element was poorly expressed in the blast population.

Figure 3:
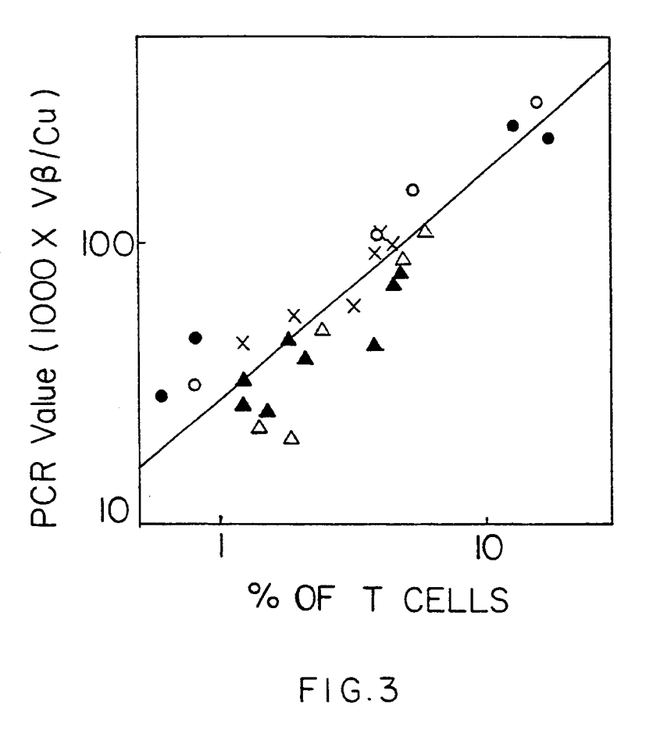
FIG. 3 depicts a standard curve used to normalize polymerase chain reaction values (PCRs) to percentages of T cells carrying particular V$\beta$s in mixed populations.

In order to test these assumptions, the actual percentage of T cell blasts expressing Vβ5.2/3, Vβ8 and Vβ12 in the various samples using flow cytometry and anti-Vβ monoclonal antibodies was determined prior to preparing mRNA. When the normalized PCR incorporations for Vβ's 5.2/3, 8 and 12 for these samples were plotted in a log/log plot against the percentage of T cell blasts staining with these anti-Vβs monoclonal antibodies, a linear relationship was obtained (FIG. 3) with the data from three different experiments indistinguishable. This relationship was most evident for values above 1%. Below about 1% Vβ expression or a normalized PCR incorporation of about 30 the correlation was lost. It was concluded, therefore that contributions from unstimulated T cells and non-productively rearranged β-genes were insignificant when Vβ expression in the blasts was greater than 1%. Therefore, the data plotted in FIG. 3 was used as a standard curve to analyze expression of Vβ's for which antibody was not used, estimating the percent Vβ expression from the normalized PCR incorporation.

Example 5

Figure 4:
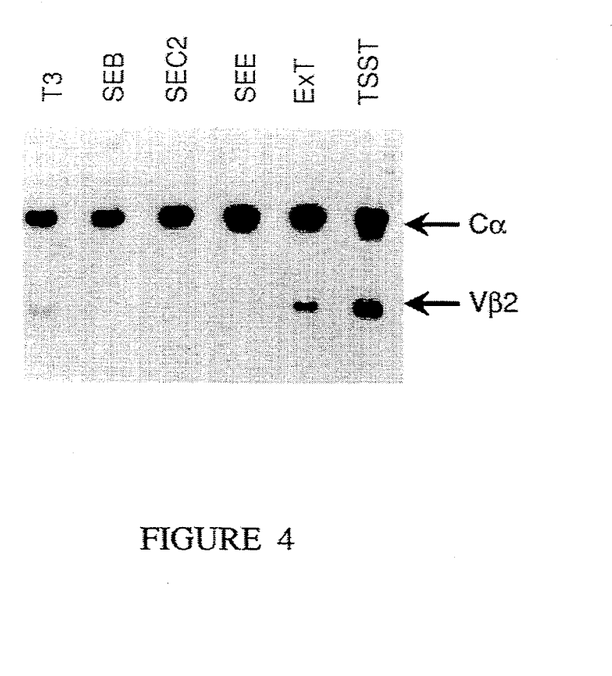
FIG. 4 shows autoradiograms of coamplified cDNA of human TCR transcripts following stimulation with anti-CD3 antibody or a S. aureus toxin.

The PCR methodology was used to analyze the expression of Vβ5.2/3, Vβ8, Vβ12 and 19 other Vβs or Vβ families in normal peripheral T cells stimulated with the various toxins. T cells stimulated with anti-CD3 were used as a control, because Examples 1 and 2 show that stimulation with anti-CD3 did not significantly change the percentages of T cells bearing particular Vβ's from that seen in the starting population. Results are shown in FIG. 4. The results of a complete analysis of the response of T cells from a single individual to five different *S. aureus* toxins are summarized in Table 3.

| | Normal T cells, % Vβ (mAbs) | Anti-CD3 Raw PCR value | % Vβ PCR | % Vβ mAbs | SEB PCR value | % Vβ PCR | % Vβ mAbs | SEC2 PCR value | % Vβ PCR | % Vβ mAbs |
|---|---|---|---|---|---|---|---|---|---|---|
| Vβ | | | | | | | | | | |
| 1 | | 88 | 3.8 | | 20 | <1.0 | | 32 | 1.1 | |
| 2 | | 180 | 9.0 | | 31 | 1.1 | | 31 | 1.1 | |
| 3 | | 156 | 7.5 | | 383 | 22.1 | | 87 | 3.7 | |
| 4 | | 57 | 2.3 | | 14 | <1.0 | | 11 | <1.0 | |
| 5.1 | | 97 | 4.3 | | 72 | 3.0 | | 26 | <1.0 | |
| 5.2–3 | 3.2 | 105 | 4.7 | 4.4 | 61 | 2.4 | 3.2 | 46 | 1.7 | 1.2 |
| 6.1–3 | | 160 | 7.8 | | 54 | 2.1 | | 88 | 3.8 | |
| 7 | | 211 | 10.8 | | 44 | 1.7 | | 89 | 3.8 | |
| 8 | 4.2 | 168 | 8.2 | 5.3 | 35 | 1.3 | 0.2 | 28 | 1.0 | 0.2 |
| 9 | | 55 | 2.2 | | 10 | <1.0 | | 29 | 1.0 | |
| 10 | | 27 | <1.0 | | 11 | <1.0 | | 16 | <1.0 | |
| 11 | | 37 | 1.3 | | 8 | <1.0 | | 11 | <1.0 | |
| 12 | 1.5 | 51 | 2.0 | 2.4 | 93 | 4.1 | 4.9 | 120 | 5.5 | 5.9 |
| 13.1 | | 181 | 9.0 | | 48 | 1.8 | | 172 | 8.5 | |
| 13.2 | | 67 | 2.7 | | 55 | 2.2 | | 115 | 5.2 | |
| 14 | | 81 | 3.4 | | 137 | 6.5 | | 157 | 7.6 | |
| 15 | | 33 | 1.2 | | 99 | 4.4 | | 94 | 4.1 | |
| 16 | | 23 | <1.0 | | 8 | <1.0 | | 13 | <1.0 | |
| 17 | | 51 | 2.0 | | 136 | 6.4 | | 123 | 5.7 | |
| 18 | | 59 | 2.4 | | 19 | <1.0 | | 14 | <1.0 | |
| 19 | | 76 | 3.2 | | 41 | 1.5 | | 22 | <1.0 | |
| 20 | | 80 | 3.4 | | 118 | 5.4 | | 186 | 9.3 | |
| Total | | | 91.2 | | | 66.0 | | | 63.1 | |

| | SEE PCR value | % Vβ PCR | % Vβ mAbs | ExT PCR value | % Vβ PCR | % Vβ mAbs | TSST PCR value | % Vβ PCR | % Vβ mAbs |
|---|---|---|---|---|---|---|---|---|---|
| Vβ | | | | | | | | | |
| 1 | 40 | 1.5 | | 37 | 1.3 | | 33 | 1.2 | |
| 2 | 41 | 1.5 | | 271 | 14.6 | | 693 | 45.0 | |
| 3 | 50 | 1.9 | | 109 | 4.9 | | 82 | 3.5 | |
| 4 | 16 | <1.0 | | 22 | <1.0 | | 80 | 3.4 | |
| 5.1 | 164 | 8.0 | | 69 | 2.8 | | 15 | <1.0 | |
| 5.2–3 | 57 | 2.3 | 1.9 | 98 | 4.3 | 3.8 | 118 | 5.4 | 4.0 |
| 6.1–3 | 263 | 14.1 | | 152 | 7.3 | | 167 | 8.2 | |
| 7 | 107 | 4.8 | | 108 | 4.9 | | 103 | 4.6 | |
| 8 | 349 | 19.8 | 15.7 | 32 | 1.1 | 0.8 | 26 | <1.0 | 0.3 |
| 9 | 5 | <1.0 | | 76 | 3.2 | | 39 | 1.4 | |
| 10 | 24 | <1.0 | | 15 | <1.0 | | 32 | 1.1 | |

-continued

| | | | | | | | | | |
|---|---|---|---|---|---|---|---|---|---|
| 11 | 11 | <1.0 | | 10 | <1.0 | | 12 | <1.0 | |
| 12 | 15 | <1.0 | 0.3 | 20 | <1.0 | 1.9 | 23 | <1.0 | 1.4 |
| 13.1 | 16 | <1.0 | | 31 | 1.1 | | 16 | <1.0 | |
| 13.2 | 33 | 1.2 | | 30 | 1.0 | | 25 | <1.0 | |
| 14 | 34 | 1.2 | | 47 | 1.8 | | 40 | 1.5 | |
| 15 | 14 | <1.0 | | 24 | <1.0 | | 26 | <1.0 | |
| 16 | 25 | <1.0 | | 12 | <1.0 | | 12 | <1.0 | |
| 17 | 29 | 1.0 | | 35 | 1.3 | | 32 | 1.1 | |
| 18 | 129 | 6.0 | | 68 | 2.8 | | 70 | 2.9 | |
| 19 | 53 | 2.1 | | 37 | 1.3 | | 35 | 1.3 | |
| 20 | 42 | 1.6 | | 39 | 1.4 | | 48 | 1.8 | |
| Total | | 67.0 | | | 55.1 | | | 82.4 | |

Some $V\beta$ families were used more abundantly than others by normal peripheral T cells. Members of the $V\beta$ 2, 3, 6, 7 and 8 families and $V\beta 13.1$ were expressed by more than 50% of total T cells. Such a finding was perhaps not unexpected for $V\beta 6$ and $V\beta 8$ which are part of large families of $V\beta$'s (although the $V\beta 6$ oligonucleotide probably primes for only 3 of the 9 members of the $V\beta 6$ family), but is more surprising for $V\beta 13.1$, which appears to be the product of a single gene. The uneven expression of $V\beta$'s by human peripheral T cells did not appear to be idiosyncratic for this individual or determined by MHC, since similar frequencies were seen for 2 other unrelated human donors tested (see discussion, infra, and FIG. 5).

Complete analysis of the expression of mRNA for all 20 families of human T cell receptor $V\beta$ genes showed clearly that all the toxins preferentially stimulated T cells expressing particular $V\beta$'s, moreover the pattern of stimulation was different for each toxin. A number of striking new associations were found. Most dramatically $V\beta 2$-bearing cells were highly-enriched by stimulation with TSST. About 50% of the T cells in TSST stimulated T cell blasts had $V\beta 2$. As was shown, supra SEB stimulated T cells bearing $V\beta 12$, but this analysis also revealed stimulation of T cells bearing $V\beta 3$, $V\beta 14$, $V\beta 15$, $V\beta 17$ and perhaps $V\beta$ 20 by SEB. The related toxin, SEC2, also stimulated T cells expressing $V\beta 12$, $V\beta 14$, $V\beta 15$, $V\beta 17$ and $V\beta 20$, but not those expressing $V\beta 3$. SEE stimulated T cells bearing members of the $V\beta 8$ family, as we have previously shown, but also increased the proportion of $V\beta 5.1+$, $V\beta 6.1-3+$, and $V\beta 18+$ cells.

Figure 5A:
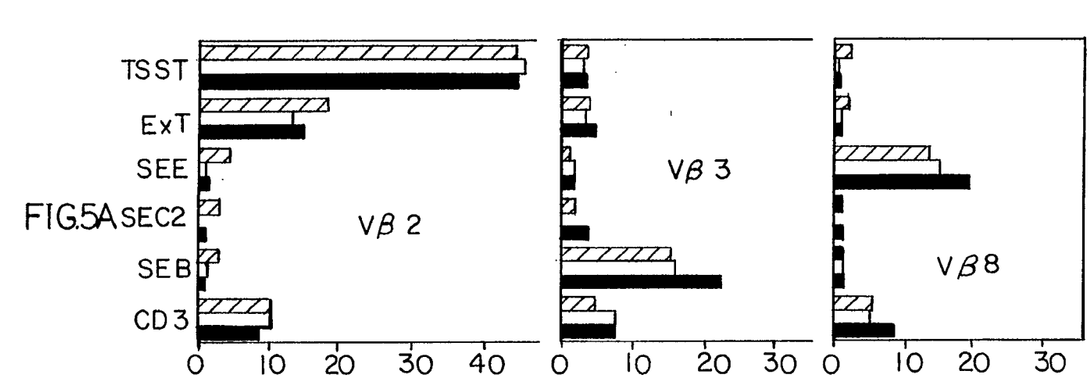
FIG. 5 presents in bar graph form V$\beta$ specific stimulation caused by S. aureus toxins in three individuals.
Figure 5B:
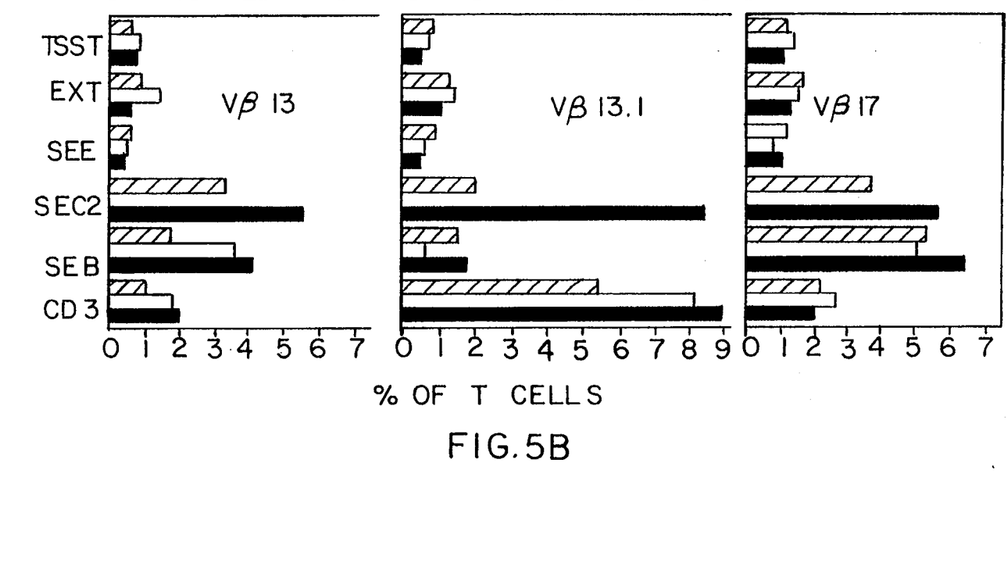

Using this method, it was possible to estimate roughly the percentage of all the T cells in a given human cell population that could be accounted for by summing those bearing the different $V\beta$s measured. As shown in Table 3, this percentage was about 90% for T cells stimulated with anti-CD3, suggesting that the estimate that the $V\beta$ oligonucleotides would prime for expression of mRNA's encoded by 39 of the 46 human $V\beta$ genes is not exaggerated, certainly not by an order of magnitude. This suggests that the 46 known $V\beta$ sequences probably cover most of the human genes. The quantitative PCR's accounted for a lower percentage of blasts stimulated by some of the toxins, in particular, ExT. It is possible that this toxin predominantly stimulates T cells bearing $V\beta$'s not covered by the listed primers Some of the most dramatic associations in Table 3 were tested in two additional human individuals to see how general the phenomena were (FIG. 5). The stimulation experiments, and calculations, were identical to those used supra. In their responses to these toxins the 3 individuals behaved almost identically. For example, $V\beta 2+$ T cells were enriched by TSST to almost the same level of 45% in every case. Similarly, in all three individuals, SEB stimulated T cells bearing $V\beta 3$ and SEE stimulated T cells bearing $V\beta 8$.

Example 6

The similarities between mice and humans in the T cell response to these toxins in striking. In both cases T cells bearing particular $V\beta$'s dominate the response to each toxin. In both cases the discriminatory powers of the toxins can be particularly dramatic. For example, in humans $V\beta 5.1+$ T cells responded to SEE, whereas cells bearing $V\beta$ 5.2/3 did not. Similarly, it has been observed by the inventors that, in the mouse, several toxins can distinguish among the members of the $V\beta$ 8 family. This member-specific response to superantigens has also been seen in mice for the endogenous superantigen, Mls-$1^a$, which stimulates T cells bearing $V\beta 8.1$ but not those expressing $V\beta 8.2$ or $V\beta 8.3$. See Kappler, et al., Nature 332: 35–40 (1988).

Extensive sequence analysis of $V\beta$ genes from mouse and man shows that there are some homologues, both by primary sequence, and by their relative location in the $V\beta$ gene complex. See Toyonaga, et al., Ann. Rev. Immunol. 5: 585–620 (1987); Concannon, et al., Proc. Natl. Acad. Sci. USA 83: 6598–6602 (1986); Lai, et al., Nature 331: 543–546 (1988). The stimulation patterns by the different toxins of these homologues by using data for mice $V\beta$ stimulation by toxins was compared, following White, et al., Cell 56: 27–35 (1989). As indicated in Table 4, in some cases T cells bearing homologous $V\beta$'s show a similar pattern of response to the toxins. ExT and especially TSST, for example, stimulated T cells bearing human $V\beta 2$ and mouse T cells bearing the most analogous $V\beta 15$. Human T cells expressing members of the $V\beta 12$, 14, 15 and 17 families all showed a tendency to respond to SEB and SEC2, but not ExT or TSST. This property was shared by their closest murine relatives, mouse $V\beta$'s 8.1, 8.2 and 8.3. However, similar response patterns by T cells bearing homologous $V\beta$'s was not always seen. For example, T cells bearing murine $V\beta 3$ responded to most of these toxins, however, those bearing the closest human analog, $V\beta 10$, did not. Even with all this information in hand, a close examination of the primary amino acid sequences of the human and mouse $V\beta$ elements has not yet revealed the essential residues responsible for toxin specificity. Thus, while tempting, complete generalization from mouse to human systems (MHC to HLA) is not indicated.

TABLE 4

Correlations Between Mouse and Human $V\beta$ Usage in Response to S. Aureus Toxins.

| | | Enriched in Response to | | | | |
|---|---|---|---|---|---|---|
| | | SEB | SEC2 | SEE | ExT | TSST |
| Mouse $V\beta$'s | 8.1 | + | ± | − | − | − |

TABLE 4-continued

Correlations Between Mouse and Human Vβ Usage in Response to *S. Aureus* Toxins.

| | | Enriched in Response to | | | | |
|---|---|---|---|---|---|---|
| | | SEB | SEC2 | SEE | ExT | TSST |
| | 8.2 | + | + | − | − | − |
| | 8.3 | + | − | − | − | − |
| Human | 14 (67) | + | + | − | − | − |
| Homologs | 12 (62) | + | + | − | − | − |
| (% Homo) | 13 (60) | − | ± | − | − | − |
| | 15 (58) | + | + | − | − | − |
| | 11 (55) | − | − | − | − | − |
| | 17 (52) | + | + | − | − | − |
| Mouse Vβ | 11 | − | − | + | − | − |
| Human | 8 (71) | − | − | + | − | − |
| Homologs | 6.1-3 (60) | − | − | + | ± | ± |
| (% Homo) | 18 (55) | − | − | + | ± | ± |
| Mouse Vβ | 15 | − | − | − | + | + |
| Human Homolog (% Homo) | 2 (45) | − | − | − | ± | + |
| Mouse Vβ | 3 | + | + | − | + | + |
| Human | 19 (67) | − | − | − | − | − |
| Homologs (% Homo) | 10 (56) | − | − | − | − | ± |

In comparing mouse and man, the most striking difference to emerge thus far in our studies is the apparent lack of mechanisms limiting Vβ expression in humans. In the mouse, despite the potential for expression of over 20 Vβ elements in the species as a whole, various mechanisms limit Vβ expression in individual mice. In some strains large genetic deletions have eliminated about half of the Vβ gene elements. See, e.g., Behlke, et al., Proc. Natl. Acad. Sci. USA 83: 767-771 (1986). Other Vβ gene elements are often inactivated by point mutations. See Wade, et al., J. Immunol. 141: 2165-2167 (1988). Most ingeniously, in many strains of mice, self-superantigens, expressed during T cell development lead to the deletion of T cells bearing particular Vβ elements during the establishment of self tolerance. See in this regard Kappler, et al., Cell 49: 273-280 (1987); Kappler, et all, Cell 49: 263-271 (1987); macDonald, et al., Nature 332: 40-45 (1988); Pullen, et al., Nature 335: 796-801 (1988); Kappler, et al., Nature 332: 35-40 (1988); Abe, et al., J. Immunol 140: 4132-4138 (1988). It is proposed that these mechanisms which lead to limited Vβ expression in individual mice may be a protective evolutionary response to the pressure exerted by bacterial toxins, so that in a population of mice some individuals will be relatively resistant to the effects of any particular toxin superantigen. No evidence for widespread similar mechanisms in humans has emerged thus far from the limited number of individuals examined. Thus large genetic deletions have not been found nor have self-superantigens which cause elimination of T cells bearing particular Vβ been observed. A closer examination both of individual members of the Vβ families and of larger human populations, especially those with a much more widespread exposure at an early age to these types of toxins, may be required to observe some of these mechanisms at work in humans.

The foregoing examples show that a pathological condition, such as an infection, can be diagnosed by assaying a sample from a patient to determine levels of particular Vβ molecules in the sample. Increased levels of specific subtypes have been found to be linked to particular antigens, as the results show.

The term "pathological condition" as used herein is not limited to an infection; rather, it refers to any condition where an abnormal immune response has occurred. This includes, e.g., autoimmune diseases where, as has been shown supra, specific Vβ type molecules are present where they should not be, or are present in quantities above those found in normal individuals.

Increases in Vβ quantities are not the only way to diagnose pathological conditions in accordance with this invention. The art is familiar with various diseases and pathological states, such as HIV infection, where T cell levels are below those normally encountered. Correlation of particular Vβ types to conditions characterized by T cell depletion are also embraced herein.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method for diagnosing a pathological condition caused by a superantigen, comprising assaying a T-cell containing body fluid sample of a human patient to determine the level of a Vβ elements characteristic of said pathological condition, and comparing the level to normal levels in a comparable T-cell containing body fluid sample, wherein a depletion of said Vβ element is indicative of a pathological condition caused by exposure to said superantigen.

2. A method for diagnosing a superantigen-mediated pathological condition, comprising assaying a T-cell containing body fluid sample of a human patient to determine the pattern of Vβ elements present, and identifying the presence of a superantigen-mediated pathological condition from said Vβ pattern.

3. A method for differentiating between superantigen-mediated pathological conditions, comprising assaying a T-cell containing body fluid sample of a human patient to determine the pattern of Vβ elements present, and identifying the specific superantigen mediating the pathological condition.

4. Method for diagnosing toxic shock syndrome comprising assaying a T-cell containing sample of a human patient to determine a level of Vβ2 subtype T cells in said sample and comparing said level to normals levels in a comparable sample, wherein an increase in said Vβ2 subtype level is indicative of toxic shock syndrome.

* * * * *

UNITED STATES PATENT AND TRADEMARK OFFICE
CERTIFICATE OF CORRECTION

PATENT NO. : 5,336,598
DATED : August 9, 1994
INVENTOR(S) : Kotzin et al.

It is certified that error appears in the above—identified patent and that said Letters Patent is hereby corrected as shown below:

Column 1, Line 53, Change "presented" to --presenting cell--

Column 1, Line 57, After "on" insert --an--

Column 2, Line 60, Change "Feed Bourne" to --Food-Borne--

Column 4, Line 32, Change "shows" to --show--

Column 4, Line 50, Change "cells" to --cell--

Column 4, Line 60, Change "nor" to --not--

Column 4, Line 63, Change "restring" to --resting--

Column 6, Line 7, Change "CD9" to --CD8--

Column 12, Line 20, Change "in" to --is--

Signed and Sealed this

Third Day of January, 1995

*Attest:*

BRUCE LEHMAN

*Attesting Officer*     *Commissioner of Patents and Trademarks*